United States Patent [19]
Marxer

[11] 3,936,359
[45] Feb. 3, 1976

[54] PROCESS FOR THE PREPARATION OF PURE DEHYDROACETIC ACID

[75] Inventor: Adrian Marxer, Visp, Switzerland

[73] Assignee: Lonza Ltd., Basel, Switzerland

[22] Filed: Jan. 25, 1974

[21] Appl. No.: 436,804

Related U.S. Application Data

[63] Continuation-in-part of Ser. No. 197,525, Nov. 10, 1971, abandoned.

[30] Foreign Application Priority Data

Dec. 1, 1970 Switzerland.................... 17752/70

[52] U.S. Cl. ..................... 203/6; 203/91; 203/41; 260/343.5
[51] Int. Cl.² ........................................ B01D 15/00
[58] Field of Search .................... 203/41, 91, 50, 6; 260/343.5, 346.1 R, 345.1, 345.6

[56] References Cited
UNITED STATES PATENTS

| | | | |
|---|---|---|---|
| 2,013,104 | 9/1935 | Macallum | 203/41 |
| 2,997,482 | 8/1961 | Craven | 260/343.5 |

OTHER PUBLICATIONS

"Unit Operations", Brown (Wiley & Sons Inc.), N.Y., 1951, pp. 398 & 399.
"Chemical Engineering Techniques", Laver, Reinhold Publishing Co., N.Y., 1952, pp. 412 & 413.

*Primary Examiner*—Norman Yudkoff
*Assistant Examiner*—Frank Sever
*Attorney, Agent, or Firm*—Christen & Sabol

[57] ABSTRACT

A process is disclosed for the purification of crude dehydroacetic acid by means of simple vacuum or reduced pressure distillation wherein activated charcoal is added to the still. The term reduced pressure is used in the sense that it excludes complicated distillations such as fractional distillation and it is synonymous with simple vacuum distillation. Preferably a pressure of about 10 to about 20 torr is maintained in the vacuum distillation still. Preferably, 0.1 to 1 percent by weight, relative to the total amount of the crude dehydroacetic acid, of activated charcoal is added to the still before the distillation occurs. Crude dehydroacetic acid, particularly that obtained from diketene, is quite impure and discolored. The process of this invention produces a pure dehydroacetic acid, which is pure white, has a transparency of 96 percent and which has a purity of greater than 99.9 percent. Data shows that when distillation is affected without activated charcoal the transparency of the resultant product is less than the crude starting material. The very pure dehydroacetic acid obtained by the process of this invention is useful as a food preservative.

14 Claims, 1 Drawing Figure

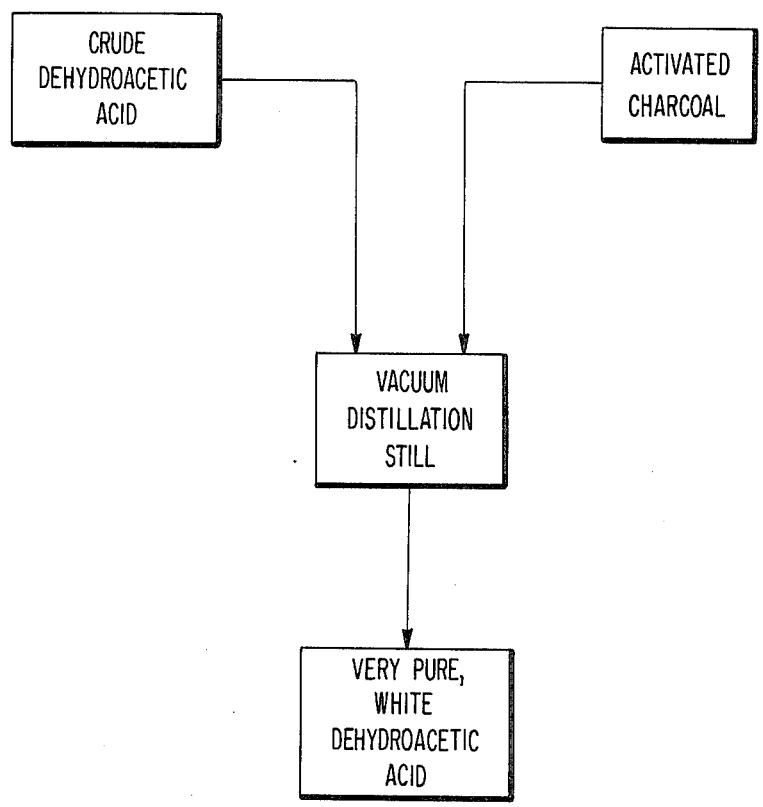

PROCESS FOR THE PREPARATION OF PURE DEHYDROACETIC ACID

This is a continuation-in-part of U.S. Ser. No. 197,525, filed on Nov. 10, 1971 now abandoned.

BACKGROUND OF THE INVENTION

1. Field of the Invention

This invention relates to the production of dehydroacetic acid and more particularily to a process of purifying dehydroacetic acid.

2. Prior Art

Several processes are known whereby dehydroacetic acid is produced from diketene. Various catalysts are available for that reaction and that reaction can be carried out in various different solvents. The dehydroacetic acid obtained in those various prior art methods, particularly if the solvent is used several times, shows very considerable discoloration. As dehydroacetic acid can be used as a food preservative, any impurities in it are undesirable, particularily colored impurities which would be visible to the consumer. Impurities are also undesirable since one of the uses of the dehydroacetic acid is in foods.

Swiss Pat. No. 362,700 describes processes for the production of dehydroacetic acid by the dimerization of diketene in an inert solvent at a temperature below 30°C., in the presence of a tertiary amine (as the catalyst) and in the absence of water. Dehydroacetic acid is crystallized; filtered out of the reaction mixture; washed with toluene; dried; and then purified by distillation after being mixed with methyl acetoacetate (specifically, see page 2, lines 11 to 15 and 42 to 54). This reference does not disclose or suggest the purification of dehydroacetic acid by means of reduced pressure or simple vacuum distillation in the presence of activated charcoal or carbon. Methyl acetoacetate acts as a co-distillant in the distillation step of this reference. The use of that, or any co-distillant, results in very serious disadvantages in the distillation purification process. An expensive distillation step and or subsequent separation scheme are needed when a co-distillant is used.

French Pat. No. 1,040,626 discloses a process for the purification of dehydroacetic acid by co-distillation of a mixture, which contains impure dehydroacetic acid and a glycol compound, at a distillation temperature of 60°C. at 1 mm pressure to 150°C. at 15 mm pressure. The process then involves crystallization to obtain the dehydroacetic acid. This reference does not disclose or suggest the purification of dehydroacetic acid by means of reduced pressure or simple vacuum distillation in the presence of activated charcoal or carbon. The glycol compound acts as a co-distillant in the distillation step of this reference. The use of that co-distillant results in very serious disadvantages in the distillation purification. An expensive distillation step and a subsequent separation scheme are needed when a co-distillant is used.

French Pat. No. 1,121,186 teaches a process for the production of dehydroacetic acid by the dimerization of diketenes. The crude dehydroacetic acid, resulting from the dimerization, is purified by distillation at an pressure of 10 to 25 mm below atmospheric pressure and using a distillation temperature between 200° and 270°C. A mixture of hydrocarbons is first added to the crude dehydroacetic acid. The hydrocarbon mixture acts as a co-distillant in the distillation step of this reference. The use of that co-distillant results in very serious disadvantages in the distillation purification process. An expensive distillation step and a subsequent separation scheme are needed when a co-distillant is used. This reference does not disclose or suggest the purification of dehydroacetic acid by means of reduced pressure or simple vacuum distillation in the presence of activated charcoal or carbon.

Swiss Pat. No. 401,086 discloses a process for the purification of dehydroacetic acid by distillation of melted dehydroacetic acid in the presence of an inert gas at a temperature of 100° to 200°C. An aromatic hydrocarbon is also present and acts as a co-distillant. Then, after liquefying the gas by the cooling thereof, dehydroacetic acid is separated out by crystallization. This reference does not disclose or suggest the purification of dehydroacetic acid by means of reduced pressure or simple vacuum distillation in the presence of activated charcoal or carbon. The use of the co-distillant in this reference results in very serious disadvantages in the distillation purification process. An expensive distillation step and a subsequent separation scheme are needed when a co-distillant is used.

Any purification process which uses a co-distillant is expensive because it requires additional processing steps after distillation to remove or separate out the co-distillant. Further, there is the added expensive of having to distill the large volume of co-distillant. Also, reduced pressure or simple vacuum distillation cannot be used when a co-distillant is admixed with the crude dehydroacetic acid. In one sense, the introduction of a co-distillant is merely the addition of large amounts of an impurity which must be subsequently removed. Examples of known co-distillants which have been used in distillation separation schemes for difficult-to-remove impurities from crude dehydroacetic acid, are methyl acetoacetate, aliphatic hydrocarbons, aromatic hydrocarbons and various glycols.

The co-distillants are additives which come off with the dehydroacetic acid and subsequently can be separated from the dehydroacetic acid. There is no chemical conversion of the co-distillate. The known co-distillates all appear to be liquids; for example, methyl acetoacetic acid is liquid at room temperatures and glycol (ethylene glycol) is a liquid at room temperature.

Attention is also drawn to U.S. Pat. Nos. 2,125,383, 2,229,204, 2,729,652, 2,849,456, 2,997,482, 3,367,847, 3,408,267, and 3,575,816; plus: Brown, "Unit Operations", Weley & Sons, Inc. (1951), pp 398 and 399; Lauer, "Chemical Engineering Techniques," Reinhold Pub. Co., (1952), pp 412 and 413; Perry et al., Chemical Engineers Handbook, 4th Ed., MccGraw-Hill, (1963), pp 16-2 to 16-5; "Rompps Chemie Lexikon," 7th Ed., Vol. 2, p. 792; "Ullmanns Enzyklopadie der Technischen Chemie," 3rd Ed., (1961), Vol. 2/1.pp. 53 and 54.

BROAD DESCRIPTION OF THIS INVENTION

This invention involves a process for the purification of crude or contaminated dehydroacetic acid. The process includes: admixing crude dehydroacetic acid and activated charcoal in a reduced pressure or simple vacuum distillation still; distilling said admixture, the distillate being vaporized, and the impurities or discoloring agents in the crude dehydroacetic acid not being vaporized and being adsorbed by the activated charcoal; and collecting the distillate, which is comprised of very pure, white dehydroacetic acid. Preferably the pressure in the still during the vacuum distillation step is maintained at between about 10 and about 20 millimeters of Hg. The process of this invention produces a dehydroacetic acid which is very white, usually has a transparency of at least 96 percent and which has a purity of greater than 99.9 percent. This pure product is obtained in the face of data which shows that, when such a distillation is conducted without the use of activated charcoal in the process, the transparency percentage of the resultant dehydroacetic acid decreases and the discoloration gets worse.

An advantage of the purification process of this invention is that it is more rapid and simpler than the known processes, and produces a more pure end product. Further, the process of this invention can utilize reduced pressure or simple vacuum distillation schemes. A very important advantage of this invention is reduced pressure or simple vacuum distillation is used to obtain very pure dehydroacetic acid from crude dehydroacetic acid without the addition of or presence of a co-distillant (also termed a retarding agent).

The very pure dehydroacetic acid obtained by the purification process of this invention is useful as a food additive and it useful in anti-enzyeme toothpastes. This is one reason why it should be pure white and contain no impurities.

If one sought to decolor crude dehydroacetic acid through recrystallization, even with the addition of decolorants such as activated carbon, one would succeed in improving the color (i.e., making the acid whiter) only with great expenditure, and would find that it is practically impossible to produce a really white dehydroacetic acid by the use of such a scheme. If one tries to purify the dehydroacetic acid by distillation, for example, using a vacuum of 10 to 20 torr, the discoloration of the distillate, as compared to the starting material, is intensified which defeats the purpose of the attempt. If the vacuum is increased, one enters the field of sublimation, which with regard to the apparatus for industrial production, leads to considerable complications and greatly increased costs.

A white dehydroacetic acid can be obtained by a distillation separation scheme using water, but the need to process (heat, distill, cool and separate) the very large volumes of water is technically and economically infeasible. The water can be replaced by lesser, yet still vast amounts of a co-distillant, such as, glycol. But the process (heat, distill, color and separate) is still technically and economically unfeasible due to the large amounts of co-distillant that have to be processed.

DETAILED DESCRIPTION OF THIS INVENTION

Dehydroacetic acid is 3-acetyl-6-methyl-1,2-pyran-2,4(3H)-dione, or dehydroacetic acid or methylacetopyronone. Dehydroacetic acid has the structural formula:

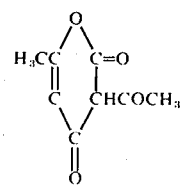

Dehydroacetic acid is a solid at room temperature.

As used herein, the term reduced pressure distillation is used in the sense that it excludes complicated distillations such as fractional distillation and it is synonymous with simple vacuum distillation. (If a co-distillant were used, fractional distillated would have to be used.) The reduced pressure or simple vacuum distillation is done in the course vacuum range (760 to 1 torr); but preferably a pressure of about 10 to about 20 torr is maintained in the vacuum distillation still, and most preferably a pressure of about 10 torr is maintained.

Perry et al., "Chemical Engineering Handbook," 3rd Ed., McGraw-Hill Book Co., Inc., (1950), at page 563, defines distillation as the separation of the constituents of a liquid mixture by partial vaporization of the mixture and separate recovery of the vapor and residue. This is exactly what this invention involves in that the liquid impurities or discoloring agents are not vaporized and are adsorbed by the activated charcoal, thereby forming part of the residue. The adsorption by activated charcoal prevents the discoloring agents from being distilled off. Prior art which uses a co-distillant apparently leaves behind the discoloring agents but achieves this only by the use of expensive fractional distillation, expensive heating and processing of the co-distillant and subsequent expensive separation of the co-distillant from the dehydroacetic acid. To have to remove one agent by the addition of another agent that subsequently has to be removed is cumbersome self-defeating in a sense and expensive. Unexpectedly, applicant is able to remove the liquid impurities in a liquid system by the addition of activated carbon in a distillation scheme. Also, unexpectedly the activated carbon adsorbs the liquid impurities instead of the dehydroacetic acid.

This invention encompasses the purification of crude dehydroacetic acid obtained from diketene acid (such processes being well known). The process usually involves dimerizing the diketene in an inert solvent at room temperature, or below, in the presence of a catalyst and in the absence of water. The catalysts are well known. Diketene or 3-buten-β lactone has the formula:

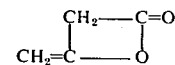

Diketene is usually prepared commercially from ketene or from bromoacetylbromide and zinc. Diketene is soluble in most common organic solvents. The solvents for diketene do not include water because water reacts with diketene.

This invention also includes the purification of crude dehydroacetic acid prepared by any method and from any starting materials. For example, it includes the purification of crude dehydroacetic acid prepared from acetoacetic ester, i.e., ethyl acetoacetate. This invention also includes the purification of contaminated dehydroacetic acid.

Any reduced pressure or simple vacuum distillation equipment (which operates in the coarse vacuum range) can be used to carry out the purification process of this invention. Preferably a pressure of about 10 to about 20 torr is maintained in the vacuum distillation still, and most preferably a pressure of about 10 torr is maintained. Typically the temperature at the head of the still will be about 135°C. Complicated distillation means such as fractional distillation means is not within the scope of this invention.

The activated charcoal can be any activated charcoal which can be used in liquid separations, as opposed to those which are used in gaseous separation. This distinction is well recognized in the literature and by those ordinarily skilled in the art. Activated charcoals are regularily sold under one or the other designation. Liquid-separation activated carbons are those in powdered form whereas gas-separation activated carbons are those in granular form. Generally the activated charcoals having the highest densities are those used for vapor adsorption. Structural hardness also plays an important role in that the vapor adsorption activated charcoals usually have high structural hardness.

The amount of activated charcoal or carbon used in the still preferably amounts to about 0.5 to about 1 percent by weight, based on the amount of crude dehydroacetic acid in the still, and most preferably about 0.7 percent by weight on the same basis.

Dehydroacetic acid purified by the method of this invention is distinguished from that purified by the prior art processes by a much higher degree of purity. Most importantly, through the addition of activated charcoal, the undesirable yellowish-brown color or tone disappears from the dehydroacetic acid (distillate) leaving it pure white.

The FIGURE is a flow diagram of the process of this invention.

The following examples illustrate but do not limit the scope of this invention. In the examples, all percentages are expressed on a weight basis, based on the weight of the crude dehydroacetic acid.

EXAMPLE 1

100 gm. of a crude dehydroacetic acid (having a transparency of 70 percent in the absorption range of 420 nm) is placed in a Claisen flask (still) having a volume of 250 ml. The temperature of the ingredients in the flask are raised to a level where distillation of product occurs, after a vacuum of 10 torr is established in the still. The temperature at the head of the still is about 135°C. The distillate (dehydroacetic acid) is collected and it weighs 98.5 gm. The distillate (dehydroacetic acid) has a strong yellow tinge or color. This, pulse the fact that the transparency of the distillate has dropped to 60 percent, established that the product is still a crude dehydroacetic acid.

EXAMPLE 2

100 gm of the same crude dehydroacetic acid as used in Example 1 (having a transparency of 70 percent in the absorption range of 420 nm) and 0.7 gm. of activated charcoal (Norit SX 1) are placed in a Claisen flask having a volume of 250 ml. "Norit SX 1" is the trade designation for a highly-adsorptive activated carbon which is commercially available from the American Norit Co. The crude dehydroacetic acid is distilled at a vacuum pressure of 10 torr. The collected dehydroacetic acid (distillate) is pure white, has a melting point which is greater than 111)C., has a transparency of 96 percent, and has a purity of greater than 99.9 percent. The distillate has the requisite solubility for pure dehydroacetic acid in aqueous ammonia. This example, when compared with Example 1, establishes the unexpected and novel advantages of using activated charcoal.

EXAMPLE 3

Crude dehydroacetic acid is prepared by the procedure described in Swiss Pat. No. 362,700. That process involves dimerizing diketene in an inert solvent at temperatures below 30°C. in the presence of a tertiary amine (as the catalyst). The dimerization is conducted in the absence of water. The crude dehydroacetic acid is crystallized out of the resultant mixture.

EXAMPLE 4

100 gm. of the crude dehydroacetic acid from Example 3 and 0.7 gm. of activated charcoal (Norit SX 1) are placed into a Claisen flask having a volume of 250 ml. The ingredients in the flask are completely admixed. The admixture in the flask is distilled under a vacuum of 10 torr. A distillate is collected which is a very pure, white dehydroacetic acid.

EXAMPLE 5

Example 2 is repeated except that a pressure of 20 torr is maintained in the still during the purification step. A distillate is collected which is a very pure, white dehydroacetic acid.

EXAMPLE 6

Example 2 is repeated except that 0.5 gm. of activated charcoal is used. A distillate is collected which is a very pure, white dehydroacetic acid.

EXAMPLE 7

Example 2 is repeated except that 1.0 gm. of activated charcoal is used. A distillate is collected which is a very pure, white dehydroacetic acid.

EXAMPLE 8

Example 2 is repeated except that the activated charcoal which is used is a liquid-separation activated charcoal which is commercially available under the trade designation "Agichar" from Agrashell, Inc. A distillate is collected which is a very pure, white dehydroacetic acid.

EXAMPLE 9

Example 2 is repeated except that the activated charcoal which is used is a liquid-separation activated charcoal which is commercially available under the trade designation "Cliffchar" (10 to 30 mesh) from the Cliffs Dow Chemical Co. A distillate is collected which is a very pure, white dehydroacetic acid.

EXAMPLE 10

Example 2 is repeated except that the activated charcoal which is used is a liquid-separation activated charcoal which is commercially available under the trade designation "Darco D-3" from Atlas Powder Co., Darco Dept. A distillate is collected which is a very pure, white dehydroacetic acid.

EXAMPLE 11

Example 2 is repeated except that the activated charcoal which is used is a liquid-separation activated charcoal which is commercially available under the trade designation "Darco G-60" from Atlas Powder Co., Darco Dept. A distillate is collected which is a very pure, white dehydroacetic acid.

EXAMPLE 12

Example 2 is repeated except that the activated charcoal which is used is a liquid-separation activated charcoal which is commercially available under the trade designation "Darco S-51" from Atlas Powder Co., Darco Dept. A distillate is collected which is a very pure, white dehydroacetic acid.

EXAMPLE 13

Example 2 is repeated except that the activated charcoal which is used is a liquid-separation activated charcoal which is commercially available under the trade designation "R-P Carbon" from Research Products Corp. A distillate is collected which is a very pure, white dehydroacetic acid.

EXAMPLE 14

Example 2 is repeated except that the activated charcoal which is used is a liquid-separation activated charcoal which is commercially available under the trade designation "Filtrex" from Stauffer Chemical Co. A distillate is collected which is a very pure, white dehydroacetic acid.

EXAMPLE 15

Example 1 was repeated, except that in order to obtain a pure white dehydroacetic acid, enough water and dehydroacetic acid were used so that there was a weight ratio of water to dehydroacetic acid of 100 to 1. The mixture of 101 parts had to be heated, distilled, cooled and separated in order to purify one part of dehydroacetic acid.

EXAMPLE 16

Example 1 was repeated, except that in order to obtain a pure white dehydroacetic acid, enough glycol and dehydroacetic acid were used so that there was a weight ratio of glycol to dehydroacetic acid of 6.5 to 1. The mixture of 7.5 parts had to be heated, distilled, cooled and separated in order to purify one part of dehydroacetic acid.

What is claimed is:

1. A process for the purification of crude dehydroacetic acid which comprises: admixing crude dehydroacetic acid and activated charcoal in a reduced pressure, simple vacuum distillation still; vacuum distilling said admixture, the distillate being vaporized, and the discoloring agents in the crude dehydroacetic acid not being vaporized and being adsorbed by the activated charcoal; and collecting the distillate, which is comprised of very pure, white dehydroacetic acid.

2. A process as described in claim 1 wherein the pressure in said still during said vacuum distillation step is maintained at between about 10 and about 20 millimeters of Hg.

3. A process as described in claim 2 wherein between 0.5 and 1 percent by weight, based on the amount of said crude dehydroacetic acid, of said activated charcoal is used in said still.

4. A process as described in claim 2 wherein about 0.7 percent by weight, based on the amount of said crude dehydroacetic acid, of activated charcoal is used in said still.

5. A process as described in claim 2 wherein said activated charcoal is powdered liquid-separation activated carbon.

6. A process as described in claim 2 wherein said still is maintained at a pressure of about 10 millimeters of Hg during said vacuum distillation step.

7. A process as described in claim 2 wherein said crude dehydroacetic acid was prepared from diketene.

8. A process for the purification of crude dehydroacetic acid which consists of: admixing crude dehydroacetic acid and activated charcoal in a reduced pressure, simple vacuum distillation still; vacuum distilling said admixture, the distillate being vaporized, and the discoloring agents in the crude dehydroacetic acid not being vaporized and being adsorbed by the activated charcoal; and collecting the distillate, which is comprised of very pure, white dehydroacetic acid.

9. A process as described in claim 8 wherein the pressure in said still during said vacuum distillation step is maintained at between about 10 and about 20 millimeters of Hg.

10. A process as described in claim 9 wherein between 0.5 and 1 percent by weight, based on the amount of said crude dehydroacetic acid, of said activated charcoal is used in said still.

11. A process as described in claim 9 wherein about 0.7 percent by weight, based on the amount of said crude dehydroacetic acid, of activated charcoal is used in said still.

12. A process as described in claim 9 wherein said activated charcoal is a powdered liquid-separation activated carbon.

13. A process as described in claim 9 wherein said still is maintained at a pressure of about 10 millimeters of Hg during said vacuum distillation step.

14. A process as described in claim 9 wherein said crude dehydroacetic acid was prepared from diketene.

* * * * *